United States Patent [19]
Toyoda et al.

[11] Patent Number: 5,270,659
[45] Date of Patent: Dec. 14, 1993

[54] APPARATUS FOR MEASURING DEPOSITION SPEED OF ELECTROLESS PLATING

[75] Inventors: Hiroyuki Toyoda; Takeshi Shimazaki, both of Ibaragi, Japan

[73] Assignees: Hitachi Chemical Company, Ltd.; Hitachi Borden Chemical Products, Inc., Tokyo, Japan

[21] Appl. No.: 777,580

[22] Filed: Oct. 16, 1991

[30] Foreign Application Priority Data

Oct. 17, 1990 [JP] Japan .................................. 2-278006

[51] Int. Cl.$^5$ .............................................. G01N 27/07
[52] U.S. Cl. .................................... 324/444; 324/425; 324/439; 324/722; 324/724; 427/8; 427/9; 427/10
[58] Field of Search ............... 324/425, 439, 444, 693, 324/699, 722, 724; 427/8, 9, 10

[56] References Cited

U.S. PATENT DOCUMENTS

| | | | |
|---|---|---|---|
| 3,824,453 | 7/1974 | Baker | 324/425 |
| 4,331,699 | 5/1982 | Suzuki et al. | 427/8 |
| 4,479,980 | 10/1984 | Acosta et al. | 427/10 |
| 4,556,845 | 12/1985 | Strope et al. | 427/10 X |
| 4,575,678 | 3/1986 | Hladky | 324/425 |
| 4,623,554 | 11/1986 | Kaschak et al. | 427/8 |
| 4,692,346 | 9/1987 | McBride et al. | 427/8 |
| 4,808,431 | 2/1989 | Rickert | 427/8 |
| 4,810,520 | 3/1989 | Wu | 427/8 |
| 4,839,580 | 6/1989 | Moore et al. | 324/699 |

FOREIGN PATENT DOCUMENTS

| | | |
|---|---|---|
| 0015548 | 9/1980 | European Pat. Off. . |
| 56-69365 | 6/1981 | Japan . |
| 58-104167 | 6/1983 | Japan . |
| 58-141373 | 8/1983 | Japan . |
| 60-130193 | 7/1985 | Japan . |
| 61-204379 | 9/1986 | Japan . |
| 62-287080 | 12/1987 | Japan . |
| 1603013 | 11/1981 | United Kingdom . |

OTHER PUBLICATIONS

An English Abstract of Japanese Laid-Open Publication No. 62-287,080, Dec., 1987.
An English Abstract of Japanese Laid-Open Publication No. 61-204,379, Sep., 1986.
An English Abstract of Japanese Laid-Open Publication No. 60-130,193, Jul., 1985.
An English Abstract of Japanese Laid-Open Publication No. 58-104,167, Jun., 1983.
An English Abstract of Japanese Laid-Open Publication No. 56-69,365, Jun., 1981.

*Primary Examiner*—Kenneth A. Wieder
*Assistant Examiner*—Glenn W. Brown
*Attorney, Agent, or Firm*—Sandler Greenblum & Bernstein

[57] ABSTRACT

An electroless plating deposition speed measuring apparatus is provided with a sensor having an electrode couple whose pair of electrodes are opposed to each other and a sensor drive circuit that cyclically applies voltage to the electrode couple to measure a polarization resistance between the pair of electrodes of the electrode couple. Measuring data from the sensor drive circuit are supplied to a processing circuit. The processing circuit computes and processes the measuring data to find the plating deposition speed. Data of the plating deposition speed from the processing circuit are supplied to a display circuit to display the data of the plating deposition speed. In a preferred embodiment, each of the pair of electrodes of the electrode couple has a conductor and a non-conductor, wherein the surfaces of the conductors and the non-conductors of the respective electrodes are arranged in facing and opposite relation to each other. Each of the conductors is made of a noble-metal material, such as copper, gold, platinum, palladium or the like, while each of the non-conductors is made of an alkaliproof non-conductive material, such as epoxy resin, epoxy resin of a glass base material, or the like.

9 Claims, 4 Drawing Sheets

(DEPOSITION SPEED MEASURING ACTION 1)

FIG.6

| NO. | COMPONENT | CONCENTRATION |
|---|---|---|
| 1 | $CuSO_4 \cdot 5H_2O$ | 10 g/l |
| 2 | $EDTA \cdot 4Na$ | 30 g/l |
| 3 | HCHO (35%) | 3.5 ml/l |
| 4 | STABILIZER | A LITTLE |
| 5 | LIQUID TEMPERATURE | 70°C |
| 6 | pH | 12.20 ~12.40 |

FIG.7

| | FLUCTUATION OF MEASURING VALUE | DIFFERENCE BETWEEN MEASURING VALUE AND DEPOSITION SPEED ON Cu FOIL |
|---|---|---|
| ELECTRODE COUPLE 20 | LESS THAN ±10% AT CONTINUOUS OPERATION FOR SIX (6) DAYS | LESS THAN ±10% AT CONTINUOUS OPERATION FOR SIX (6) DAYS |
| ELECTRODE COUPLE 20B | EQUAL TO OR GREATER THAN ±10% AT OPERATION FOR ONE (1) DAY | EQUAL TO OR GREATER THAN ±10% AT OPERATION FOR ONE (1) DAY |

APPARATUS FOR MEASURING DEPOSITION SPEED OF ELECTROLESS PLATING

BACKGROUND OF THE INVENTION

The present invention relates to an apparatus for measuring a deposition speed of electroless plating liquid.

Conventionally, in a manufacturing step of a printed control panel or distributing board, an electroless copper plating step occupies the important position. Importance of the electroless copper plating step increases more and more with development of an additive process. The reason for this is that, when a plating thickness is not set to an adequate value, defects occur in the quality aspect. For example, in the case where the plating thickness is large, a problem of etching leavings occurs in the subsequent pattern forming step. To the contrary, in the case where the plating thickness is conversely thin, problems such as occurrence of cracks and the like arise, which causes the through-hole reliability to be reduced.

In order to prevent such deficiencies, it is necessary to control the plating thickness to an adequate value. As a measuring method of controlling the plating thickness, there is a weight method in which a weight of plated copper, which is deposited for a predetermined period of time, for example, for thirty (30)~sixty (60) minutes, is measured. Since, however, this measuring method must detect the weight of the copper periodically, there are disadvantages that it becomes difficult to continue the measurement, and to bring the measurement to an apparatus.

In view of the above, as a technique for removing the above-described disadvantages, in recent years, there has been proposed, in Japanese Laid Open Patent Publication No. SHO 58-141373 or the like, a method for measuring a deposition speed of the electroless plating liquid by means of a polarization resistance process. This is a method which is characterized in that, when electroless copper plating reaction advances on a pair of copper electrodes, in electroless plating liquid, under conditions that electrical potential is Ep1 and a deposition speed is lp1, a constant or predetermined electric current $\Delta I$ is given from the outside in accordance with the following relational expression, and an outside polarization $\Delta E$ induced thereby is measured:

$$\mathrm{lp1} = K \cdot \frac{\Delta I}{\Delta E} \tag{1}$$

where
$\Delta E$ is the outside polarization;
$\Delta I$ is the outside current; and
K is a constant determined by the reaction condition.

In the method described above, however, not only is the apparatus complicated in structure and more expensive, but also the surface of the dissolved metal is apt to be oxidized. Accordingly, there are problems that it is difficult to effect plating onto the electrode surfaces, and it becomes difficult to effect correct or accurate measurement.

In fact, experiments conducted by the inventors of the present application enabled the results in which fluctuation of a measurement value was brought to $\pm 20\%$ or more per two (2) days, to be obtained.

In connection with the above, in the experiments, electroless copper plating liquid L-59 is used which is manufactured by Hitachi Chemical Co. Ltd.

As described above, when the fluctuation of the measurement value is brought to $\pm 20\%$ or more, it is not possible to control the correct or accurate plating thickness. Etching leavings and cracks occur in the measuring step of the printed control panel. This reduces the through-hole reliability considerably.

SUMMARY OF THE INVENTION

It is therefore an object of the invention to provide an apparatus for measuring a deposition speed of electroless plating, in which a difference between a measuring value and a deposition speed of a metal foil such as copper or the like is small, and fluctuation of the measuring value is also small.

In order to achieve the above-described object, according to the invention, there is provided an apparatus for measuring an electroless plating deposition speed, comprising:

a sensor having an electrode couple whose pair of electrodes are opposed to each other;

a sensor drive circuit for cyclicly applying voltage to the electrode couple to measure a polarization resistance between the pair of electrodes of the electrode couple;

a processing circuit for inputting measuring data from the sensor drive circuit, computing and processing the measuring data to find the plating deposition speed; and a display circuit for displaying data of the plating deposition speed supplied from the processing circuit.

In a preferred embodiment, each pair of electrodes of the electrode couple has a conductor and a non-conductor. The surfaces of the conductors and the non-conductors of the respective electrodes are arranged in facing and opposite relation to each other. Each of the conductors is made of a noble-metal material such as copper, gold, platinum, palladium or the like. Each of the non-conductors is made of an alkaliproof non-conductive material such as epoxy resin, epoxy resin of a glass base material, or the like.

With the arrangement of the invention, voltage is applied to the pair of electrodes by the sensor drive circuit. When the voltage is applied, the polarization resistance between the pair of electrodes is measured, while, when the voltage is not applied, the electroless plating is deposited on the electrode couple.

The polarization resistance is outputted to the processing circuit as a voltage value, and is converted into a digital signal. Subsequently, the converted output is used to compute the deposition speed of the electroless plating components at the computing section. The results of the computation are displayed by the display circuit.

In this manner, in the present invention, since the deposition speed is computed and displayed on the basis of the polarization resistance between the pair of electrodes, accurate continuous measurement of the deposition speed is made possible so that a difference between the actual deposition speed and the measuring value is reduced to the utmost.

Further, in the preferred embodiment, since the conductive material of each of the pair of electrodes is made of a noble-metal material such as gold, platinum or the like which is small in ionization series, the metal surface is prevented from being oxidized. As a result, plating of each of the electrode surfaces advances smoothly. Thus, the measurement of the deposition speed, which is higher in accuracy, is made possible.

The construction or arrangement of the pair of electrodes in the preferred embodiment will be described below. The case where a metal material is formed on the inside opposed surfaces of the pair of electrodes is compared with the case where the metal material is formed on the outside opposite surfaces of the pair of electrodes. The former has a tendency that the diffusing condition of the plating liquid is made more uniform, while the latter has a tendency that the diffusing condition of the plating liquid is made non-uniform. For this reason, the arrangement in which the metal material is formed on each of the inside opposed surfaces is less in difference between the measuring value and the deposition speed on the copper foil than the arrangement in which the metal material is formed on each of the outside opposite surfaces. Furthermore, fluctuation of the measuring value is also reduced.

Moreover, each of the non-conductive surfaces is made of a non-conductive material of alkalinity such as an epoxy resin material or the like, whereby deterioration of the non-conductive surface is reduced and, in addition thereto, an attempt can be made to recycle the pair of electrodes. The service life of the pair of electrodes is also considerably prolonged.

BRIEF DESCRIPTION OF THE DRAWINGS

FIG. 6 is a view showing components of electroless copper plating liquid which is used in measurement of a deposition speed of copper at plating processing; and FIG. 7 is a view showing the results in which the apparatus according to the embodiment of FIG. 1 is used to measure the deposition speed of copper at plating processing, in comparison with a comparative example.

DETAILED DESCRIPTION OF THE PREFERRED EMBODIMENTS

Figure 1:
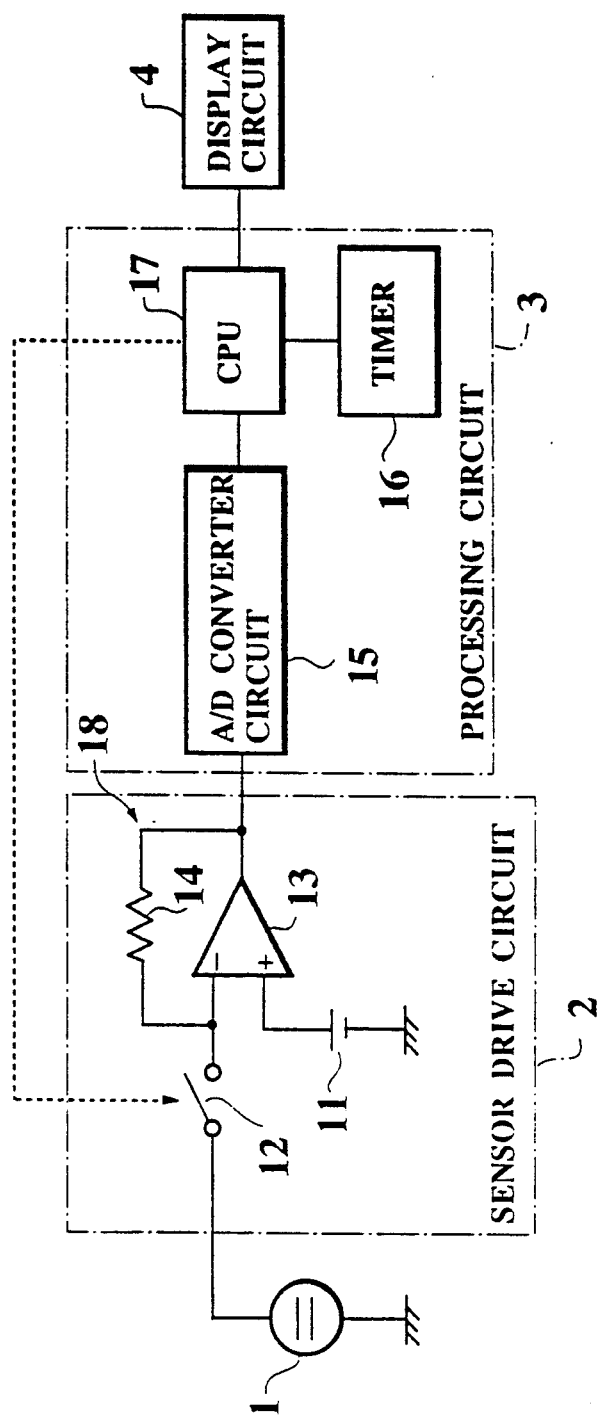
FIG. 1 is a block diagram showing an embodiment of an apparatus according to the present invention for measuring a deposition speed of electroless plating.

FIG. 1 is a block diagram showing an embodiment of an apparatus for measuring a deposition speed of electroless plating, according to the present invention.

The apparatus for measuring the deposition speed of electroless plating, illustrated in FIG. 1, comprises a sensor 1, a sensor drive circuit 2, a processing circuit 3 and a display circuit 4. A signal obtained due to driving of the sensor 1 by the sensor drive circuit 2 is processed to find a deposition speed. The deposition speed is displayed by the display circuit 4.

The sensor drive circuit 2 comprises an electric source 11 for generating a reference voltage of preferably 5 mV~20 mV, a switch 12 for applying the reference voltage obtained by the electric source 11 to the sensor 1 to take out a current signal flowing at the application of the reference voltage, and a current/voltage converting circuit 18 having an operational amplifier 13 and a resistance 14 for converting the current signal taken out by the switch 12 to a voltage signal. The generated voltage signal is supplied to the processing circuit 3.

The processing circuit 3 comprises an A/D converter circuit 15, a timer 16 and a CPU 17. The processing circuit 3 operates the switch 12 with a predetermined cycle to apply the voltage to a pair of electrodes 19a and 19b (shown in FIG. 2) of the sensor 1. A voltage signal outputted from the sensor drive circuit 2 at this time is processed to find a plating deposition speed. The plating deposition speed is displayed by the display circuit 4.

The A/D converter circuit 15 A/D-converts the voltage signal outputted from the sensor drive circuit 2 to generate voltage data which are supplied to the CPU 17.

Further, the timer 16 effects time operation to generate time data which are supplied to the CPU 17.

The CPU 17 switches the switch 12 so as to be brought to a predetermined cycle, for example, to a cycle such that a ratio between energization time and deenergization time with respect to the sensor 1 is brought to a range of from 1:1 to 1:10, on the basis of the time data obtained by the timer 16, to apply the voltage to the electrodes 19a and 19b of the sensor 1, or to apply no voltage thereto.

Furthermore, when the voltage is applied to the electrodes 19a and 19b of the sensor 1, the CPU 17 processes the voltage data outputted from the A/D converter circuit 2 in accordance with the following operational equation to find the plating deposition speed which is supplied to the display circuit 4:

$$E_o = K \cdot E_s \cdot R_f 1/R_p \qquad (2)$$

where

K is a constant;

$E_o$ is a value of the voltage data;

$E_s$ is a value of reference voltage outputted from the electric source 11;

$R_f$ is a value of the resistance 14 within the current-/voltage converting circuit 18; and $1/R_p$ is a polarization conductance of the sensor 1.

In this case, since the constant K, the value $E_s$ of the reference voltage outputted from the electric source 11, and the value $R_f$ of the resistance 14 in the equation (2) are brought to their respective predetermined values, the polarization conductance $1/R_p$ of the sensor 1 is found from the value $E_o$ of the voltage data, and the plating deposition speed is found from the polarization conductance $1/R_p$. The plating deposition speed is supplied to the display circuit 4.

When the plating deposition speed is supplied from the CPU 17, the display circuit 4 displays the plating deposition speed.

Specifically, for example, SSR, A2P/202A manufactured by JEL SYSTEM Co., Ltd. is used as a relay drive section for driving the switch 12, LT-13741 manufactured by NATIONAL CONDUCTOR Co., Ltd. is used as the operational amplifier 13 of the current/voltage converting circuit 18, CICL-7109 manufactured by MAXIM Co., Ltd is used as the A/D converter circuit 15, HLIC 6340 manufactured by HITACHI Co., Ltd. is used as the timer 16, and HL 6309E manufactured by HITACHI Co., Ltd. is used as the CPU 17.

In addition the elements described above, connected to the CPU 17 are, for example, a contact output section [Trade Name: HL-6321, manufactured by HITACHI Co., Ltd.] which functions as means for outputting a warning or alarm and the like, a panel input-output section [Trade Name: μPC 8279C, manufactured by NIHON ELECTRIC Co., Ltd.] for displaying input and output of data to and from the CPU, a D/A converting section [Trade Name: MT-7528, manufactured by MAXIM Co., Ltd.] for creating a signal for a recorder, a conductance measuring section [Trade Name: LF-13741, manufactured by NATIONAL CONDUCTOR Co., Ltd.] for measuring conductance, and the like (all not shown).

Figure 2:
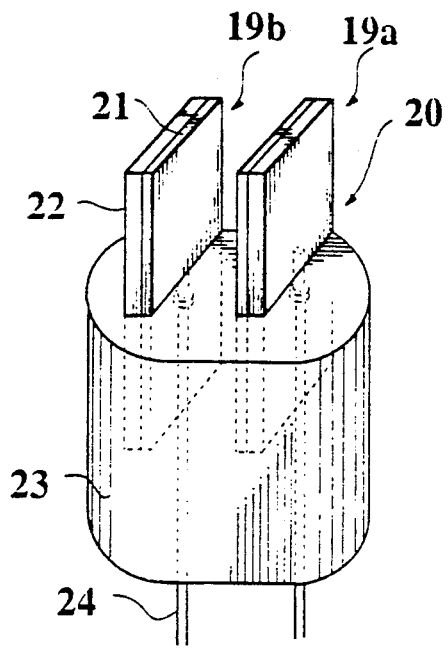
FIG. 2 is a perspective view showing an electrode couple of a sensor provided in the embodiment of FIG. 1.

The sensor 1 has an electrode couple 20 as shown in FIG. 2. The electrode couple 20 is provided with the aforementioned pair of electrodes 19a and 19b. The pair of electrodes 19a and 19b have their respective surfaces which are opposed to each other. Conductive surfaces 21 are formed respectively on the opposed or facing surfaces, and non-conductive surfaces 22 are formed respectively on the opposite surfaces. Preferably, each of the conductive surfaces 21 is made of a noble-metal material such as copper (Cu), gold (Au), platinum (Pt), palladium (Pd) or the like. Preferably, each of the non-conductive surfaces 22 is made of an alkaliproof non-conductive material such as epoxy resin, epoxy resin of a glass base material, or the like.

These electrodes 19a and 19b are fixedly supported by epoxy resin 23. A pair of lead wires 24 extend through the epoxy resin 23, and have their respective forward ends connected respectively to the conductive surfaces 21. The lead wires 24 are covered with Teflon (Trademark).

Figure 3:
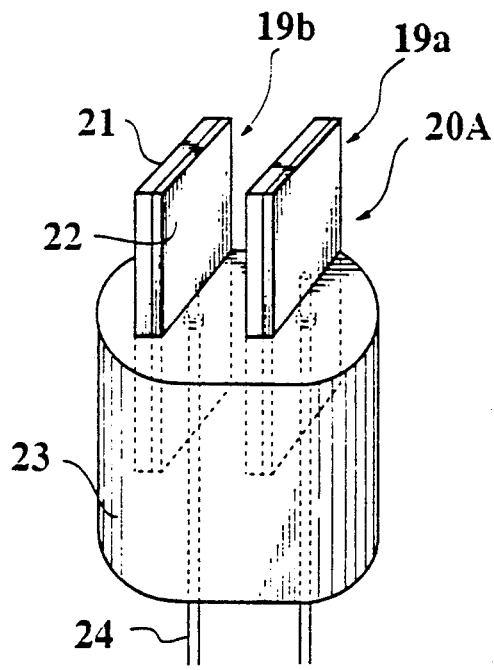
FIGS. 3 and 4 are perspective views showing modifications of the electrode couple.
Figure 4:
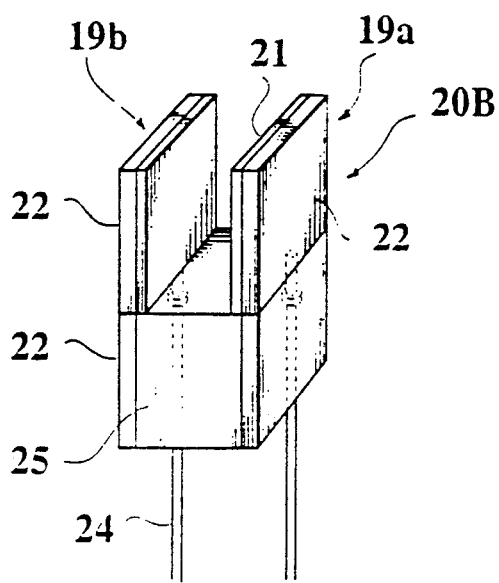

FIGS. 3 and 4 show respectively modifications of the electrode couple. An electrode couple 20A shown in FIG. 3 has a pair of electrodes 19a and 19b which are arranged such that the non-conductive surfaces 22 are opposed to each other. An electrode couple 20B has a pair of electrode 19a and 19b by which an element 25 of a rectangular parallelepiped, made of polypropylene, is clamped.

Figure 5:
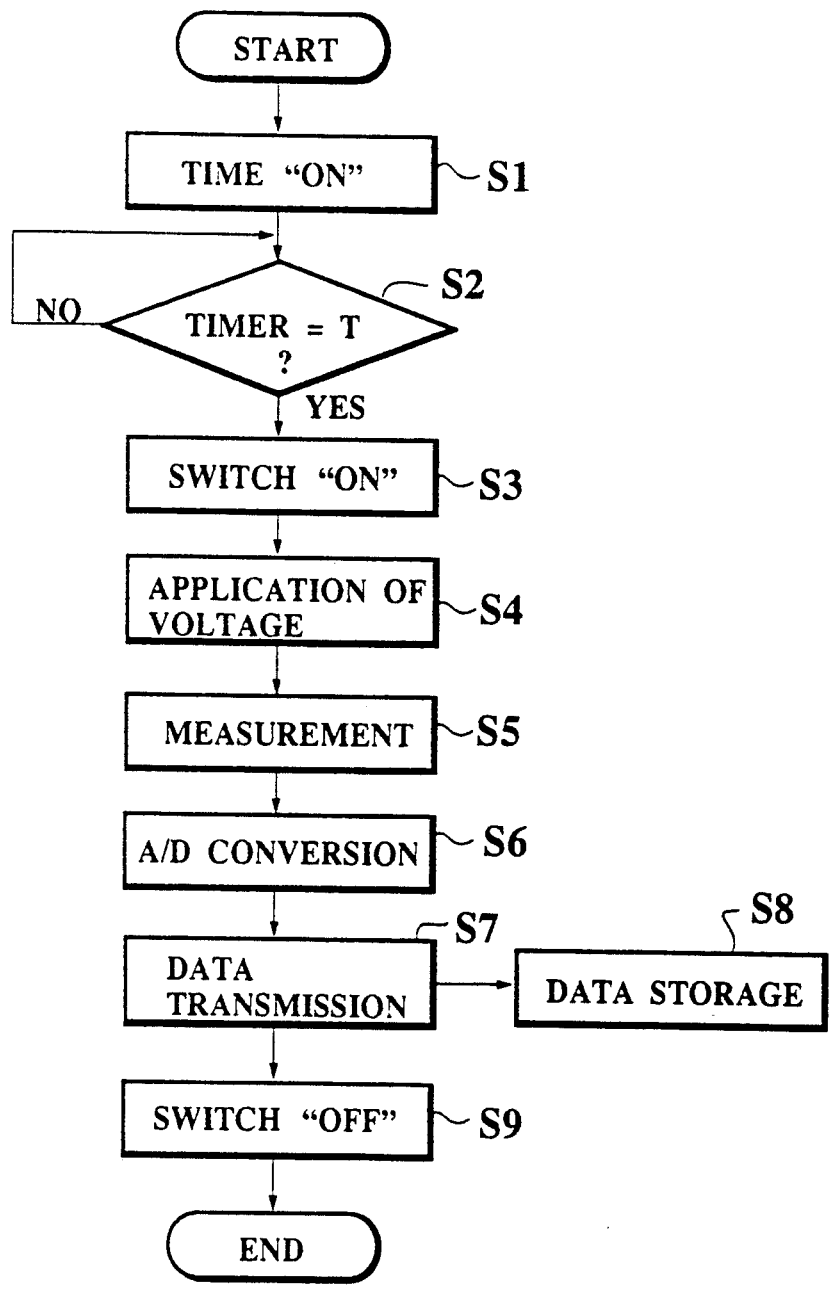
FIG. 5 is a flow chart showing an operation of measuring the deposition speed, in the embodiment of FIG. 1.

Measuring action or operation of the embodiment will next be described with reference to FIG. 5.

In the measuring apparatus illustrated in FIG. 1, a timer section is first turned on to start measurement (step S1). Then, the change-over switch 12 is turned off for six seconds after start of the measurement (step S2). After six seconds have been elapsed, the change-over switch 12 is turned on for the first time (step S3), so that the voltage is applied to the electrode couple 20.

Subsequently, after the voltage has been applied to the electrode couple (step S4), a polarization conductance (inverse number of a polarization resistance value) is measured (step S5). Measured analog data are converted into digital data by the A/D converter circuit 15 (step S6). Converted data are transmitted to the CPU 17, and are stored in a memory section (steps S7 and S8). Subsequently, the change-over switch 12 is turned "OFF" (step S9), whereby the measurement of the deposition speed is completed. Such operation is repeated.

At this time, output voltage obtained by the sensor drive circuit 2 changes or varies as follows. That is, when plating is made to the surfaces of the respective electrodes 19a, 19b of the electrode couple 20 and voltage is applied to the surfaces of the respective electrodes 19a, 19b, a polarization conductance occurs between the pair of electrodes 19a, 19b of the electrode couple 20.

The voltage varies by polarization resistance occurring at this time, and the variation in the voltage is measured. Here, the plating speed has a proportional relationship with respect to the polarization conductance, because the following relational expression (3) holds:

$$1p1 = K \frac{1}{RP} \quad (3)$$

where
1p1 is the plating speed;
K is a constant; and
1/RP is the polarization conductance.

Further, the voltage has a proportional relationship with respect to the polarization conductance, because the voltage has the following relational expression (4):

$$EO = E_s \cdot R_f \cdot \frac{1}{RP} \quad (4)$$

where
EO is output voltage;
$R_f$ is a feedback resistance; and
RP is a polarization resistance.

For the reason discussed above, the voltage is measured, whereby it is possible to measure the plating speed.

The apparatus of the aforementioned embodiment is next used to compare, with each other, the results in which the deposition speed of copper is measured at plating processing. Measurement was conducted in which the electrode couple 20 or 20B illustrated in FIGS. 2 and 4 were dipped in electroless copper plating liquid containing components illustrated in FIG. 6.

The case where the electrode couple 20 is used and the case where the electrode couple 20B is used, in the apparatus according to the embodiment, are shown in FIG. 7 in comparison.

In the above-described experiment, a fluctuation value at each of intervals of ten minutes was investigated regarding fluctuation of the measuring value. Further, the deposition speed was investigated on the basis of a change in plating thickness per one hour.

As will be seen from FIG. 7, the following good or superior results were obtained. That is, in the electrode couple 20B, the fluctuation of the measuring value, and a difference between the measuring value and the deposition speed of the copper foil were both brought to a value equal to or greater than ±10% in spite of operation for only one day, whereas, in the electrode couple 20, the fluctuation and the difference were both brought to a value less than ±10% even if operation was conducted continuously for six days.

Furthermore, since the non-conductive surface of the electrode couple 20 is made of an epoxy resin material, it is made possible to use the apparatus in a recycling manner.

In connection with the above, in the aforesaid measuring action for the deposition speed, the measuring cycle was short, for example, for ten seconds, and a four seconds application time of the voltage with respect to the electrodes and a six second processing time of electroless plating were alternately repeated, whereby it was possible to approach the real time. Further, when the voltage is applied to the electrodes 19a, 19b, reading of the conductance data can start after an elapse of two seconds from the time the voltage has been applied, in order to lose or nullify the charging time with respect to the condenser component of the electrodes.

In the apparatus for measuring the present electroless deposition speed, according to the invention, the construction and material of the electrode couple have been such that modifications of various types such as the electrode couple 20, 20A or 20B were considered as shown in FIG. 2, 3 or 4. According to the experiments, however, superior or good results were obtained if the former electrode couple 20 is used, more than the case of the latter two electrodes 20A and 20B. That is, it has been known that, by the use of the electrode couple 20 illustrated in FIG. 2, a difference between the measuring value and the deposition speed on the copper foil decreases, and fluctuation of the measuring value decreases. Furthermore, it has also been known that, if, after constant copper has been deposited on the conductive surface, the copper is removed, it is possible to again use the electrode couple, that is, it is made easy to use the electrode section in a recycling manner.

At present, a factor of a difference of the measuring results due to the electrode couples 20 and 20A is unknown. According to the inventors of the present application, however, it has perhaps been considered that the difference is a difference in chemical reaction of the plating liquid in the electrode surface due to the diffusion condition.

Moreover, a difference in measuring results due to the electrode couples 20 and 20B is considered such that, when the electrode couples are dipped in high-temperature and high-alkali liquid, leakage occurs because a close-contact force between the conductive surface and the Teflon material is reduced, so that copper is gradually deposited or precipitated at a contact section between the conductive surface and the lead wires, whereby a difference between the measuring value and the deposition speed on the copper foil increases and, in addition thereto, fluctuation of the measuring value increases.

What is claimed is:

1. An apparatus for measuring an electroless plating deposition speed, comprising:
    a sensor comprising an electrode couple whose pair of electrodes face each other, each of said electrodes of said electrode couple having a conductor and a non-conductor on an inside portion and an outside portion, respectively, of each of said electrodes, each of said conductors being made of a noble-metal material, and each of said non-conductors being made of an alkaliproof non-conductive material;
    a sensor drive circuit that cyclically applies a single reference voltage to said electrode couple and measure a voltage proportional to a polarization resistance between said pair of electrodes of said electrode couple when the reference voltage is applied to said electrode couple, an electroless plating being deposited on said electrode couple when the reference voltage is not applied;
    a processing circuit that inputs the measured voltage from said sensor drive circuit and computes the electroless plating deposition speed; and
    a display circuit that inputs data of the plating deposition speed from said processing circuit and displays the data of the plating deposition speed.

2. An apparatus for measuring an electroless plating deposition speed according to claim 1,
    wherein said noble-metal material includes one of copper, gold, platinum and palladium, and said alkaliproof non-conductive material includes one of epoxy resin and epoxy resin of a glass base material.

3. An apparatus for measuring an electroless plating deposition speed according to claim 2,
    wherein said pair of electrodes of said electrode couple are fixably supported by a base member made of epoxy resin, and a pair of lead wires extending through said base member are connected respectively to said conductors.

4. An apparatus for measuring an electroless plating deposition speed according to claim 3,
    wherein said pair of electrodes are arranged such that a surface of each of said conductors face toward each other.

5. An apparatus for measuring an electroless plating deposition speed according to claim 1,
    wherein said sensor drive circuit applies the reference voltage to said electrode couple in a cycle having a ratio between energization time and deenergization time that is substantially within a range from 1:1 to 1:10.

6. An apparatus for measuring an electroless plating deposition speed according to claim 1,
    wherein said processing circuit computes the polarization resistance between said pair of electrodes of said electrode couple based on the measured voltage in accordance with a first predetermined relational expression, and computes the electroless plating speed based on the computation of the polarization resistance in accordance with a second predetermined relational expression.

7. An apparatus for measuring an electroless plating deposition speed according to claim 6,
    wherein said first predetermined relational expression is a relational expression between the polarization resistance and the measured voltage, and said second predetermined relational expression is a relational expression between the electroless plating deposition speed and the polarization resistance.

8. An apparatus for measuring an electroless plating deposition speed according to claim 6,
    wherein said first predetermined relational expression is:

$$Eo = K \cdot Es \cdot Rf(1/Rp)$$

where $Eo$ the measured voltage, $K$ is a constant, $Es$ is the reference voltage, $Rf$ is a feedback resistance of the sensor drive circuit, and $Rp$ is the polarization resistance.

9. An apparatus for measuring an electroless plating deposition speed according to claim 6,
    wherein said second predetermined relational expression is:

$$lpl = K(1/Rp)$$

where $lpl$ is the electroless plating deposition speed, $K$ is a constant, and $Rp$ is the polarization resistance.

* * * * *

UNITED STATES PATENT AND TRADEMARK OFFICE
CERTIFICATE OF CORRECTION

PATENT NO. : 5,270,659
DATED : December 14, 1993
INVENTOR(S) : H. TOYODA et al.

It is certified that error appears in the above-indentified patent and that said Letters Patent is hereby corrected as shown below:

At column 7, line 3, delete "present".
    At column 7, line 4, insert ---present--- before "invention".

Signed and Sealed this

Twenty-sixth Day of July, 1994

Attest:

BRUCE LEHMAN

*Attesting Officer*     *Commissioner of Patents and Trademarks*